United States Patent [19]

Heaven et al.

[11] Patent Number: 5,330,483
[45] Date of Patent: Jul. 19, 1994

[54] SPECIMEN REDUCTION DEVICE

[75] Inventors: Malcolm D. Heaven, Hopewell; Michael Schuler, Edison, both of N.J.

[73] Assignee: Advanced Surgical Inc., Princeton, N.J.

[21] Appl. No.: 992,776

[22] Filed: Dec. 18, 1992

[51] Int. Cl.5 ............................................. A61B 17/22
[52] U.S. Cl. ...................................... 606/114; 606/127
[58] Field of Search .............. 606/127, 128, 201, 220, 606/203, 191, 198, 110, 114; 604/104, 113; 128/DIG. 25

[56] References Cited

U.S. PATENT DOCUMENTS

| | | | |
|---|---|---|---|
| 4,512,338 | 4/1985 | Balko et al. | 606/108 |
| 4,553,545 | 11/1985 | Maass et al. | 604/104 |
| 4,556,050 | 12/1985 | Hodgson et al. | 128/DIG. 25 |
| 4,655,771 | 4/1987 | Wallsten | 606/198 |
| 4,739,762 | 4/1988 | Palmaz | 606/108 |
| 5,037,379 | 8/1991 | Clayman et al. | 600/37 |
| 5,037,427 | 8/1991 | Harada et al. | 606/108 |
| 5,074,867 | 12/1991 | Wilk | 606/128 |
| 5,139,480 | 8/1992 | Hickle et al. | 606/191 |
| 5,147,371 | 9/1992 | Washington et al. | 606/127 |
| 5,201,901 | 4/1993 | Harada et al. | 606/198 |

Primary Examiner—Tamara L. Graysay
Attorney, Agent, or Firm—Burns, Doane, Swecker & Mathis

[57] ABSTRACT

A medical device and method of using the device such as during laparascopic procedures for reducing the size of specimens so that they can be removed from the body by a minimally invasive surgical technique. The device is thermally activated and is useable in conjunction with or as part of a tissue isolation bag. The device includes an inner wall defining an empty space for receiving surgically removed tissue. The member is in an expanded condition at body temperature but shrinks to a smaller specimen reducing configuration wherein the empty space becomes smaller when the member is heated to a temperature above body temperature. By careful selection of the material for the specimen reduction device, a range of specific shrink temperatures may be obtained which are suitable for use within the body. For example, the member can be of a shape memory metal or a shape memory polymer.

15 Claims, 2 Drawing Sheets

SPECIMEN REDUCTION DEVICE

BACKGROUND OF THE INVENTION

1. Field of the Invention

The invention relates to a medical device useful during laparascopic procedures for reducing the size of specimens so that they can be removed from a body by a minimally invasive surgical technique.

2. Description of Related Art

During the removal of a diseased gallbladder, an inflamed appendix, or other procedure using laparoendoscopic techniques it is frequently necessary to remove objects which are larger than the tubular structure (e.g., trocar) through which the procedure is being conducted. One method of reducing the size of such object is to use a device such as a morcellator, which, in conjunction with a suitable tissue isolation bag, mechanically reduces the size of the object by a grinding or flailing action. The isolation bag can then be subsequently withdrawn through the trocar. If such a device is not available, or is ineffective, then the surgeon must increase the size of the hole through which he is working, which is not desirable. The current invention offers a much improved method of tissue or stone reduction.

U.S. Pat. No. 5,037,379 ("Clayman") discloses a surgical tissue bag for percutaneously debulking tissue by inserting the bag through an access sheath into a body cavity, inserting surgically removed tissue through an open end of the bag, closing the end of the bag and pulling the closed end out of the body cavity, opening the end of the bag and morcellating or debulking the tissue through the open end of the bag while the remainder of the bag remains in the body cavity. The bag is made of flexible and foldable material and includes an inner layer of puncture resistant material such as nylon in either a woven or solid layer form for resisting penetration by a surgical morcellating instrument. The outer layer of the bag is made of a moisture proof material such as plastisol.

U.S. Pat. No. 5,074,867 ("Wilk") discloses a procedure for removing a gall bladder wherein a sheet-like membrane having wires connected to corners thereof is used to remove the gall bladder. The gall bladder may or may not be pre-crushed by means of a crushing forceps prior to pulling on the wires to cover the gall bladder and remove the membrane and gall bladder from the patient.

U.S. Pat. No. 5,037,427 ("Harada") discloses a stent made of a bidirectional shape memory alloy such as nickel-titanium (Ni-Ti) binary alloy, copper-aluminum-nickel (Cu-Al-Ni) ternary alloy or copper-zinc-aluminum (Cu-Zn-Al) ternary alloy. The stent has a small diameter at 15° C. and lower and has a larger diameter at body temperature (about 35° to 37° C.). The stent can be formed of spirally wound flat wire, a longitudinally split cylindrical tube, a net in the form of a cylindrical tube, or a cylindrical tube. In use, the stent is shrunk onto a catheter tube, the catheter is introduced into a tubular organ while cooling the stent with ice-cooled physiologic saline, the stent is heated by heat of the living body and the stent expands into contact with the inner wall of the tubular organ.

SUMMARY OF THE INVENTION

The invention provides a thermally activated specimen reduction device which includes a member having an inner wall defining an empty space for receiving and reducing in size surgically removed tissue. The member is initially in an expanded configuration at body temperature but can be shrunk to a smaller specimen reducing configuration wherein the empty space becomes smaller by heating the member to a temperature above body temperature. Preferably, the inner wall of the member exerts a crushing force sufficient to crush a tissue specimen when the member shrinks from the expanded configuration to the smaller specimen reducing configuration.

In accordance with various aspects of the invention, the member can be made from various materials and have various shapes. For instance, the member can be of flexible material which is collapsible to a size small enough to be inserted into a human body cavity through a trocar. The member can be in the shape of a tubular structure, a tubular braided structure, a coil or comprise a tube of material having a cut therethrough extending spirally between opposite ends of the tube. Also, the member can be comprised of heat recoverable metal or polymer material in the form of fiber, wire, sheet, tube or other shape.

The device can further include a tissue isolation bag and the device can be discrete from the isolation bag or incorporated in a wall of the isolation bag. For instance, the isolation bag can be made of a heat recoverable material and the member can comprise a sidewall of the isolation bag.

The invention also provides a method of removing surgically removed tissue from a living body wherein the device is used to reduce the size of the tissue prior to removing the device and tissue from a body cavity such as through a trocar.

DETAILED DESCRIPTION OF THE PREFERRED EMBODIMENTS

The invention relates to a new and improved device for reducing the size of specimens whereby such specimens can be removed by a less invasive technique. The device will be useful in the field of laparoscopic cholecystectomy and related procedures.

When a tissue sample or, for example, a gallbladder containing an excessively large stone is required to be removed from a patient's body, there are currently no really convenient ways of achieving this. As such, it is common to increase the size of the wound site to allow retrieval. This to some extent defeats the objective of using a minimally invasive surgical technique to remove such tissue. The invention provides a device and method of using the device to overcome this drawback.

The invention offers considerably improvement over existing methods of removing specimens from a patient. In particular, the invention provides a thermally activated specimen reduction device 1 useable in conjunction with or as part of an isolation bag 2, as shown in FIGS. 1-5.

According to one preferred embodiment of the invention, the device 1 can comprises a braided tubular member 1a comprised of heat recoverable fiber, which may be polymer or shape memory metal fibers. Suitable fibers may be made from, but are not limited to, fibers manufactured from ultra-high molecular weight polyethylene in the case of a polymer, or nickel titanium alloy in the case of a shape memory metal alloy. In both instances the tubular structure is in the expanded configuration prior to use, and may be recovered to its desired small size by the application of heat. In both instances, the recovery forces are substantial, and as the material shrinks to its small size it will compact or crush whatever it contains.

Suitable polymer fiber materials which can be used to manufacture the member include polycaprolactone, polycaprolactone blends and copolymers, polyethylene terephthalate and copolymers thereof, engineering polymers such as polyether ketone or polyether ether ketone. By careful selection of the material for the specimen reduction device, a range of specific shrink temperatures may be obtained which are suitable for use within the body. For example, a particular polycaprolactone has a crystalline melting point of 47° C., which is a safe temperature to use within the abdominal cavity should the risk of significant organ contact exist.

Figure 3:
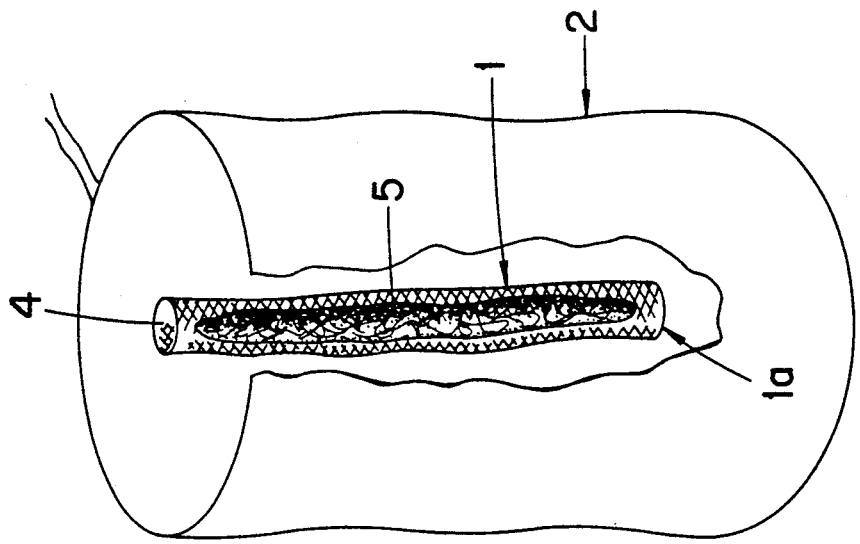
FIG. 3 shows the device of FIG. 2 after shrinking, whereupon the contained specimen has been severely crushed and reduced in size.
Figure 2:
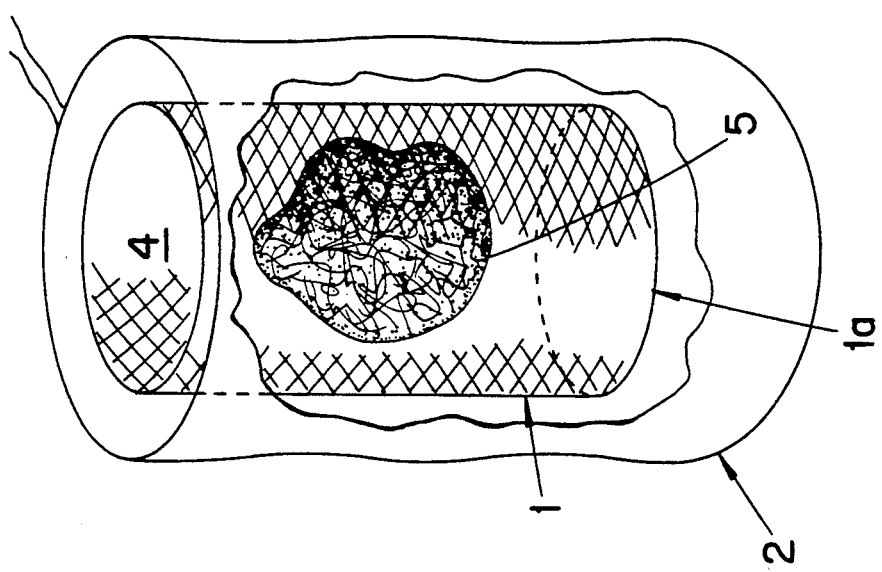
FIG. 2 shows a specimen such as a stone or piece of tissue inserted into the inside of the device of FIG. 1.
Figure 1:
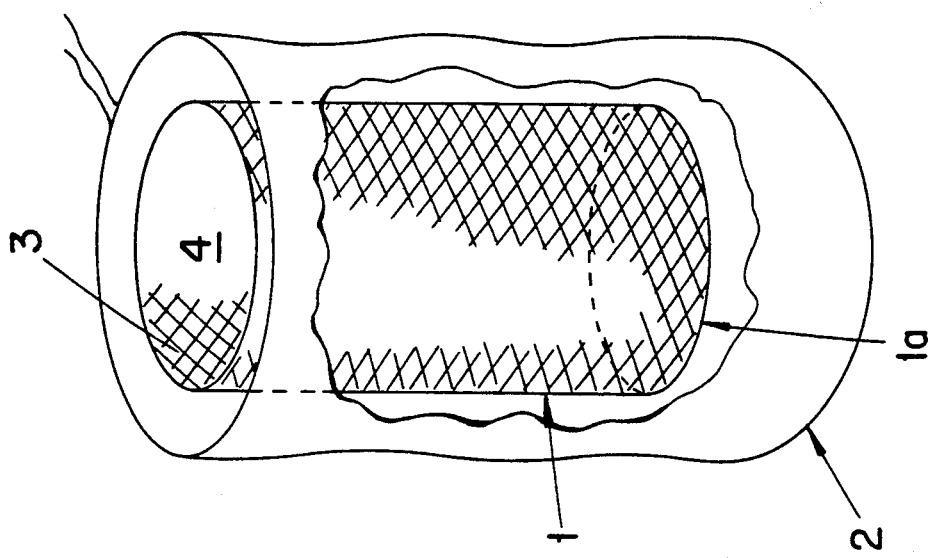
FIG. 1 shows a tubular thermally activated specimen reduction device in an isolation bag in accordance with the invention.
Figure 4:
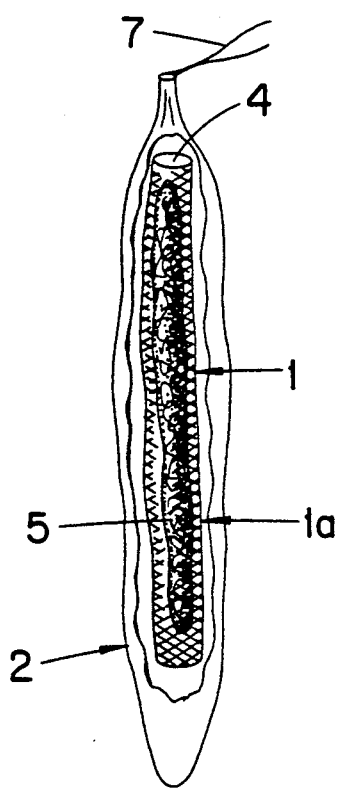
FIG. 4 shows the neck of the isolation bag of FIG. 3 drawn tightly closed in preparation for removal.
Figure 5:
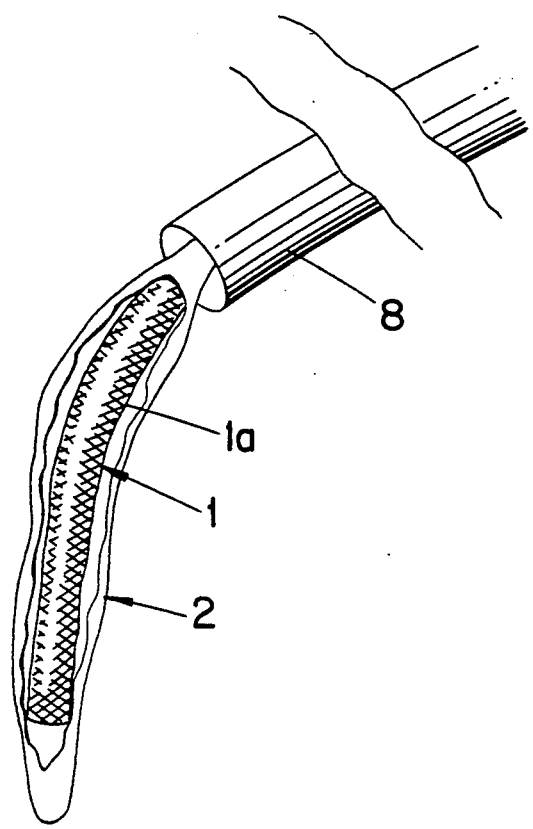
FIG. 5 shows the isolation bag of FIG. 4 and contents therein being withdrawn through a trocar.

As shown in FIGS. 1-5, the device 1 comprises a braided tubular member 1a which includes an inner wall 3 defining an empty space 4 for receiving surgically removed tissue 5. The member is in an expanded condition at body temperature (as shown in FIGS. 1 and 2) but shrinks (via thermal activation) to a smaller specimen reducing configuration (as shown in FIGS. 3-5) wherein the empty space becomes smaller when the member is heated to a temperature above body temperature.

The device 1 can be thermally activated by means of a heat source such as hot liquid. Alternatively, the device 1 can be heated by passing electricity directly through the member or through a material in contact with the member. For instance, the braided member 1a can be made of NiTi alloy wire or a polymer fiber having an electrically conductive formulation.

Figure 6:
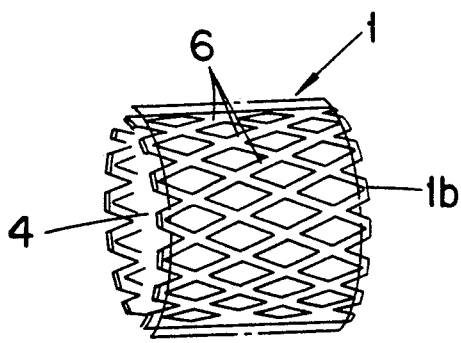
FIGS. 6–9 show embodiments of a shrinkable device in accordance with the invention wherein the device is made from tubing having a pattern of longitudinal slits (FIGS. 6 and 7) or from a coil of material (FIGS. 8 and 9).
Figure 7:
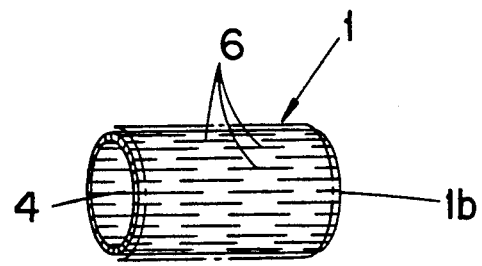

According to a second embodiment of the invention, the device 1 can comprise a tubular member made of one of the heat recoverable materials described with reference to the first embodiment of the invention. For example, the member can comprises a tube 1b with a pattern of longitudinal slits 6 therein. The slits 6 can be cut by suitable methods known to those skilled in the art (e.g., laser cutting, etc.) to give a shape such as that shown in FIGS. 6 and 7. Cutting the tube in this way allows greater movement with NiTi structures, but is not absolutely necessary with heat or electrically shrinkable polymers since they inherently have more expansion capability. In use, the tubular member 1b shrinks from the expanded configuration in FIG. 6 to the smaller configuration in FIG. 7. In order to provide a tubular member 1b in a ready-to-use condition, the member 1b can be heated above a transformation temperature of the particular shape memory material involved, expanded from the smaller configuration shown in FIG. 7 to the expanded configuration shown in FIG. 6, and cooled while held in the expanded configuration.

Figure 8:
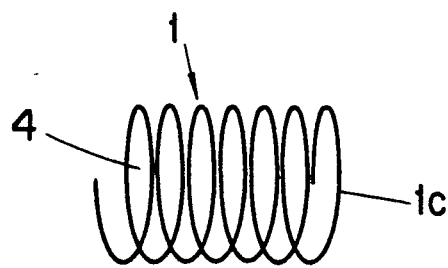
Figure 9:
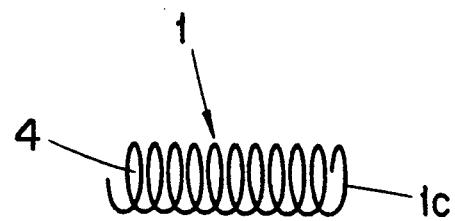

Another possible shape of the member is the coil 1c shown in FIGS. 8 and 9. The coil 1c shown in FIG. 8 shrinks when heated above body temperature from the expanded configuration in FIG. 8 to the smaller configuration in FIG. 9. As in the other embodiments, the member 1c can be initially formed with dimensions corresponding to the smaller specimen reducing size of the member, heated and enlarged to an expanded specimen receiving size, and cooled while retaining the member in the ready-to-use expanded configuration.

To prevent escape of diseased material into, e.g., the abdominal cavity, the specimen reducing device can be operated within a suitable tissue isolation bag such as that described in co-pending and commonly assigned U.S. patent application Ser. No. 07/797,727, the subject matter of which is hereby incorporated by reference.

A further advantage of the specimen reducing device is that it can be readily folded for insertion and removal through, e.g., a standard trocar. For instance, in order to remove the device from the abdominal cavity of a living human body, a drawstring 7 of the isolation bag can be drawn to close the bag 2 (as shown in FIG. 4) and the bag 2 can be pulled out of a body cavity through a trocar 8, as shown in FIG. 5.

According to a further embodiment, the device can be incorporated within the wall of the isolation bag. In this case, the device would enhance deployment of the isolation bag and the specimen reduction device, and on recovery would assist collapse of the isolation bag. According to yet a further embodiment of the invention, the isolation bag could be made from heat shrinkable material which will reduce in size while crushing a specimen upon application of heat to the device.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A thermally activated specimen reduction device comprising:
 a member having an inner wall defining an empty space for receiving surgically removed tissue, the member being in an expanded configuration at body temperature, and the member being shrinkable from the expanded configuration to a smaller specimen reducing configuration wherein the empty space becomes smaller, the member shrinking to the small configuration by heating the member to a temperature above body temperature, the inner wall of the member exerting a crushing force when the member shrinks from the expanded configuration to the smaller specimen reducing configuration, and the crushing force being sufficient to crush the surgically removed tissue.

2. The thermally activated device of claim 1, wherein the member is of flexible material which is collapsible to a size small enough to be inserted into a human body cavity through a trocar.

3. The thermally activated device of claim 1, wherein the member is in the shape of a tubular structure.

4. The thermally activated device of claim 1, wherein the member is in the shape of a tubular braided structure.

5. The thermally activated device of claim 1, wherein the member is in the shape of a coil.

6. The thermally activated device of claim 1, wherein the member is comprised of heat recoverable fiber.

7. The thermally activated device of claim 1, wherein the member is comprised of a heat recoverable metal.

8. The thermally activated device of claim 1, the member is comprised of a heat recoverable polymer material.

9. The thermally activated device of claim 1, wherein the device further includes a tissue isolation bag.

10. The thermally activated device of claim 9, wherein the device is discrete from the isolation bag.

11. A method of reducing the size of tissue and removing it from a living body, comprising steps of:

introducing a thermally activated specimen reduction device into a living body, the device having an inner wall defining an empty space for receiving surgically removed tissue, the member being in an expanded configuration at body temperature, and the member being shrinkable from the expanded configuration to a smaller specimen reducing configuration wherein the empty space becomes smaller, the member shrinking to the small configuration by heating the member to a temperature above body temperature;

placing tissue surgically removed from the body into the empty space while the member is in the expanded configuration;

heating the member to a temperature above body temperature and shrinking the member to the specimen reducing configuration while reducing the tissue in the empty space to a smaller size; and withdrawing the device and tissue from the body while the device is in the specimen reducing configuration.

12. The method of claim 11, wherein the member is of flexible material which is collapsible to a size small enough to be inserted into a human body cavity through a trocar, the introducing step being performed by passing the member through a trocar and into a human body cavity.

13. The method of claim 11, wherein during the heating step the inner wall of the member exerts a crushing force as the member shrinks from the expanded configuration to the specimen reducing configuration, the crushing force being sufficient to crush the tissue.

14. The method of claim 11, further comprising introducing a tissue isolation bag into the body, the heating step performed while the member is in the isolation bag and the withdrawing step being performed by withdrawing the bag from the body.

15. The method of claim 14, wherein the device is discrete from the isolation bag.

* * * * *